(12) United States Patent
Weber et al.

(10) Patent No.: US 11,254,629 B2
(45) Date of Patent: Feb. 22, 2022

(54) OLIGOMERIZATION REACTOR WASH PROCESS USING BY-PRODUCT SOLVENT RECOVERED USING A THIN FILM EVAPORATOR

(71) Applicant: ExxonMobil Chemical Patents Inc., Baytown, TX (US)

(72) Inventors: Michael W. Weber, Houston, TX (US); Larry L. Iaccino, Seabrook, TX (US); Keith H. Kuechler, Friendswood, TX (US); John S. Coleman, Houston, TX (US); Jay L. Reimers, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/908,014

(22) Filed: Jun. 22, 2020

(65) Prior Publication Data
US 2021/0017104 A1    Jan. 21, 2021

Related U.S. Application Data

(60) Provisional application No. 62/875,646, filed on Jul. 18, 2019.

(51) Int. Cl.
*C07C 7/00* (2006.01)
*B01J 19/24* (2006.01)
*C07C 2/08* (2006.01)

(52) U.S. Cl.
CPC .......... *C07C 7/005* (2013.01); *B01J 19/2465* (2013.01); *C07C 2/08* (2013.01); *B01J 2219/00033* (2013.01)

(58) Field of Classification Search
CPC ... C07C 7/005; C07C 2/08; C07C 7/04; B01J 19/2465; B01J 2219/00033; Y02P 20/582
See application file for complete search history.

(56) References Cited

U.S. PATENT DOCUMENTS

| 5,728,912 A * | 3/1998 | Saqualain Haider Rizvi ............. C07C 2/08 502/126 |
| 8,524,972 B1 | 9/2013 | Weber et al. ................. 585/809 |
| 8,658,750 B2 | 2/2014 | Lattner et al. ................. 526/352 |
| 10,370,307 B2 | 8/2019 | Boutrot et al. ........... C07C 2/08 |
| 2010/0036185 A1* | 2/2010 | Yokoyama ................ C07C 2/32 585/510 |
| 2018/0009728 A1* | 1/2018 | Emoto ...................... C08F 6/12 |
| 2018/0179122 A1* | 6/2018 | Boutrot ................ B01J 19/2465 |

FOREIGN PATENT DOCUMENTS

WO    WO2012/072178    6/2012    ............. B01J 19/00

* cited by examiner

*Primary Examiner* — Ali Z Fadhel

(57) ABSTRACT

A method for washing an oligomerization reactor using by-product solvent recovered from the reactor can include: catalytically converting a monomer in a reactor section in a reaction mode in the presence of a catalyst to form a product stream comprising an oligomer, a by-product solvent, and a polymeric by-product; separating the product stream into a first fraction comprising the oligomer and a second fraction comprising a mixture of the by-product solvent and the polymeric by-product; and separating, in a thin film evaporator, the second fraction into a third fraction comprising the by-product solvent and a fourth fraction comprising the polymeric by-product.

16 Claims, 2 Drawing Sheets

OLIGOMERIZATION REACTOR WASH PROCESS USING BY-PRODUCT SOLVENT RECOVERED USING A THIN FILM EVAPORATOR

CROSS-REFERENCE OF RELATED APPLICATIONS

This application claims priority to and the benefit of U.S. Provisional Application No. 62/875,646, filed Jul. 18, 2019, the disclosure of which is incorporated herein by reference.

FIELD

The present disclosure relates generally to systems and methods for catalytically converting a monomer to an oligomer during which a polymeric by-product may be formed.

BACKGROUND

Linear alpha olefins are a valuable chemical product that can be produced within a reactor vessel by the oligomerization of the olefin monomer ethylene. In many cases, oligomerization processes form polymer as a by-product, and this polymeric by-product commonly fouls the oligomerization reactor.

As an example of the complications of oligomerization, 1-hexene can be produced in high selectivity via ethylene trimerization using homogeneous, single-site chromium catalyst systems, activated by a molar excess of alkyl aluminums such as methyl alumoxane (MAO) and modified methyl alumoxane (MMAO). In an unavoidable side reaction, a small fraction of the converted ethylene forms polyethylene as a by-product. This polymeric by-product can take any or all of the following three forms: (i) it can coat surfaces of the reactor and associated piping; (ii) it can flow out of the reactor in solution with the reaction mixture; or (iii) it can flow out of the reactor as a suspended solid in the reaction mixture. In addition, the formation of polymer can continue downstream of the reaction system due to the presence of the still-active catalyst in the reactor product stream or effluent.

The build-up of a polymeric by-product that remains within the oligomerization reactor itself and in associated reactor piping can be troublesome. After polymer by-products like polyethylene have fouled internal reactor surfaces and piping, it may become necessary to shut down the reactor(s) and clean the reactor(s) and piping. Shutting down of the reactor(s) for cleaning and maintenance is, of course, economically disadvantageous because production of the desired oligomerization product is interrupted. Some conventional solutions include periodically introducing a suitable wash liquid or utility solvent, such as an alcohol, to flush a shut-down reactor and piping to remove the built-up by-products. The use of a separate utility solvent requires additional tankage and piping to introduce this extra material to the process. In addition to this capital expenditure, operation outlays are increased to purchase the utility solvent. Removal or recovery of this utility solvent from the process equipment for disposal or re-use also requires additional energy and equipment.

SUMMARY OF THE DISCLOSURE

The present disclosure relates generally to systems and methods for catalytically converting a monomer to an oligomer during which a polymeric by-product may be formed. More specifically, the present disclosure relates to using an oligomer process that also forms another by-product that may be used as a solvent for removing a polymeric by-product from a reactor or other equipment.

A method in accordance with this disclosure may comprise catalytically converting a monomer in a reactor section in a reaction mode in the presence of a catalyst to form a product stream comprising an oligomer, a by-product solvent, and a polymeric by-product; separating the product stream into a first fraction comprising the oligomer and a second fraction comprising a mixture of the by-product solvent and the polymeric by-product; and separating, in a thin film evaporator, the second fraction into a third fraction comprising the by-product solvent and a fourth fraction comprising the polymeric by-product.

A system in accordance with this disclosure may comprise: a reactor section being configurable to operate under oligomerization conditions for a monomer in the presence of a catalyst to form a product mixture comprising an oligomer and a by-product solvent, and a polymeric by-product from the monomer; a separation unit fluidically coupled to receive the product mixture from the reactor; and a thin film evaporator (TFE) fluidically coupled to receive fluid from the separation unit.

Another method in accordance with this disclosure may comprise: catalytically converting a monomer in a reactor section in a reaction mode in the presence of a catalyst to form a product stream comprising an oligomer, a by-product solvent, and a polymeric by-product; and separating the product stream into a first fraction and a second fraction; wherein, the first fraction comprises a first portion of the by-product solvent and the oligomer, and the second fraction comprises a second portion of the by-product solvent and the polymeric by-product. The method may further comprise: passing the first fraction through a separation section to extract the first portion of the by-product solvent; passing the second fraction through a thin film evaporator to extract the second portion of the by-product solvent; and delivering the first and second portions of the by-product solvent to the reactor section in a wash mode.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
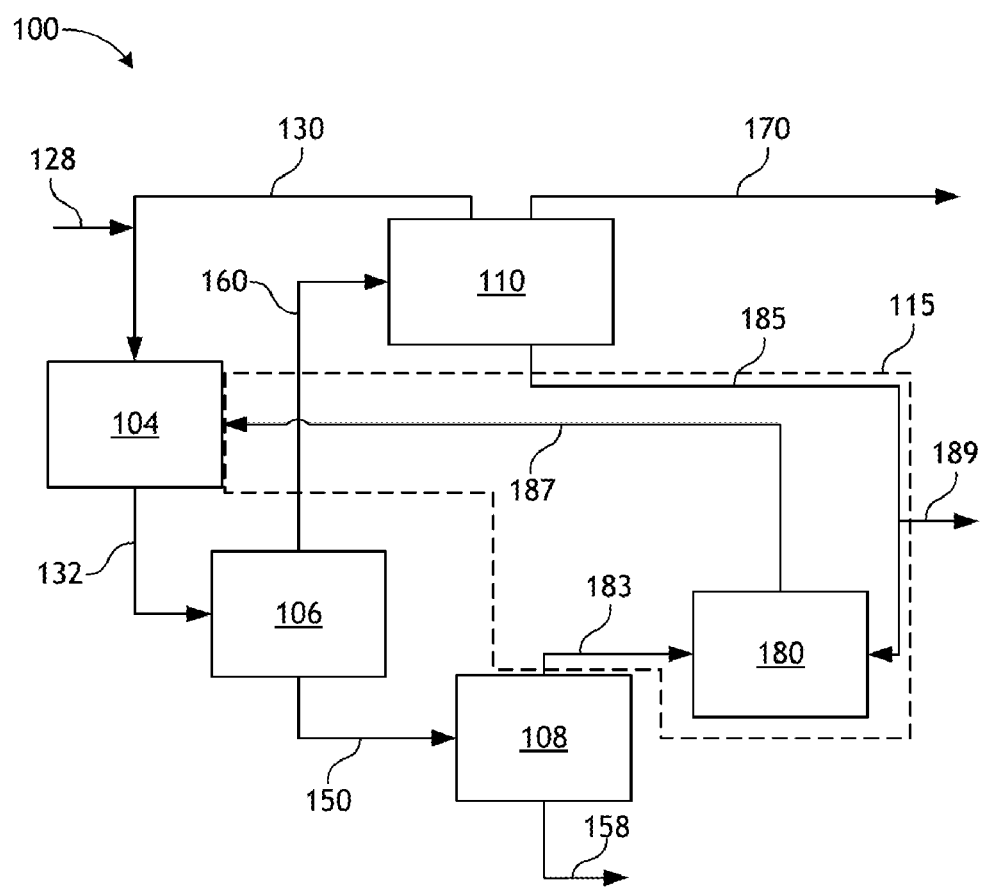
FIG. 1 shows a diagram of a system demonstrating various operations that may be performed in the course of converting monomer to oligomer according to various embodiments of the present disclosure.

The present disclosure relates generally to systems and methods for catalytically converting a monomer to an oligomer during which a polymeric by-product may be formed. More specifically, the present disclosure relates to an oligomer process that also forms a second by-product that may be used as a solvent for removing a polymeric by-product from a reactor or other equipment. The disclosed processes extract and periodically or intermittently recycle to the reactor this second by-product, which will be called a solvent by-product.

In view of the known difficulties, which can arise in dealing with catalyst and polymeric by-products found in the reactor product stream from a conventional olefin oligomerization processes, it would be advantageous to provide procedures and apparatus configurations for efficiently and cost-effectively separating catalyst material and polymeric by-products from the process equipment and from the remainder of the product stream. The procedures, apparatus, systems, and processes disclosed herein are believed to provide these or other benefits.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Ordinal numbers such as first, second, third, etc. do not indicate a quantity but are used for naming and reference purposes. In addition, ordinal numbers used in the claims in reference to a component or feature may differ from the ordinal numbers used in the written description for the corresponding component or feature. For example, a "second object" in a claim might be described as a "third object" or may be described without an ordinal number in the written description.

For the sake of clarity, not all features of a physical embodiment are described or shown in this application. It is understood that in the development of a physical embodiment incorporating the embodiments of the present disclosure, numerous implementation-specific decisions must be made to achieve the developer's goals, such as compliance with system-related, business-related, government-related, and other constraints, which vary by implementation and from time to time. While a developer's efforts might be time-consuming, such efforts would be, nevertheless, a routine undertaking for those of ordinary skill in the art and having benefit of this disclosure.

Oligomerization Systems and Methods

FIG. 1 shows a diagram of a system 100 demonstrating various operations that may be performed in the course of catalytically converting a monomer to an oligomer. System 100 is suitable for olefin oligomerization, such as the trimerization of ethylene into hexene.

Although system 100 is presented such that the catalytic conversion of a monomer to an oligomer is accomplished via a flow process, which may involve a steady flow process, it is to be appreciated that the concepts presented herein may also be implemented as a batch process in alternative embodiments.

System 100 includes a reactor section 104 fluidically coupled to a separation unit 106, a thin film evaporator (TFE) 108 fluidically coupled to separation unit 106, a separation section 110 fluidically coupled to separation unit 106, and a solvent flow path 115 that fluidically couples TFE 108 and separation section 110 to reactor section 104.

Reactor section 104 includes one or more reactors (preferably two or more reactors for steady operation outside the reactor section 104) configured to operate under oligomerization conditions for a monomer in the presence of a catalyst to form an oligomer and a by-product solvent from the monomer. In at least some examples, reactor section 104 is configured for operation in which the monomer includes ethylene, the oligomer includes hexene, and the by-product solvent includes decene.

A feed line 128 and a reactant return line 130 are fluidically coupled to reactor section 104. A line 132 fluidically couples reactor to a downstream separation unit 106. Separation unit 106 may also be described as separation section and in some embodiments may include a plurality of separation units. A line 150 fluidically couples separation unit 106 to thin film evaporator 108. TFE 108 is fluidically coupled to a by-product discharge line 158, which may be connected, fluidically coupled to a related process or may lead to storage or shipment equipment.

Returning to separation unit 106, a line 160 fluidically couples separation unit 106 to separation section 110. Separation section 110 may include one or more separation units. Reactant return line 130 fluidically couples separation section 110 to reactor 104. Separation section 110 is fluidically coupled to a product discharge line 170, which may be fluidically coupled to a related process or may lead to storage or shipment equipment.

Continuing to reference FIG. 1, solvent flow path 115 fluidically couples TFE 108 and reactor section 104. Another portion of solvent flow path 115 fluidically couples separation section 110 and reactor section 104. System 100 and solvent flow path 115 are configured to deliver intermittently by-product solvent from TFE 106 or separation section 110 to reactor section 104. Solvent flow path 115 of FIG. 1 is configured to blend solvent discharged by TFE 108 with by-product solvent discharged by separation section 110. Solvent flow path 115 includes a collection vessel 180. Solvent flow path 115 further includes a line 183 that fluidically couples collection vessel 180 to TFE 108, a line 185 that fluidically couples collection vessel 180 to separation section 110, and a solvent recycle line 187 that fluidically couples collection vessel 180 to reactor 104. A solvent discharge line 189 may fluidically couple solvent flow path 115 to a related process or may lead to storage or shipment equipment. Discharge line 189 is coupled to line 185 to allow by-product solvent and perhaps other fluids from separation section 110 to be removed from system 100. Discharge line 189 may be operated to allow the passage of a continual stream or may be operated in an intermittent, blow-down mode. Thus, solvent flow path 115 includes collection vessel 180 fluidically coupled between TFE 108 and reactor section 104 and fluidically coupled between the separation section 110 and reactor section 104. Solvent flow path 115 may include a valve in solvent recycle line 187 to control the flow of solvent from collection vessel 180 to reactor section 104 to stop, start, or modulate that flow of solvent.

The operation of process or system 100 includes a process that involves sequential implementations of a reaction mode of operation and a wash mode of operation for a selected reactor (or reactors) in reactor section 104. Even so, the net flow of product from reactor section 104 preferably remains constant in some examples as one or more reactors continue in the reaction mode while one or more reactors operate in the wash mode. The cycling between reaction mode and wash mode may be a continuous process, for example. During the reaction mode of operation, a catalyst and a reactant, which includes a monomer, are provided to the selected reactor in reactor section 104 via feed line 128. Optionally, solvent corresponding to the by-product solvent may also be introduced via feed line 128. The monomer may be provided by a continuous or intermittent flow. A catalyst may also be fed via feed line 128, along with the monomer. In reactor section 104, monomer in the presence of the catalyst is converted to form a product stream comprising an oligomer, a by-product solvent, and a polymeric by-product. The product stream is delivered to separation unit 106 via line 132. In separation unit 106, the product stream is separated into a first fraction, which exits through line 160, and a second fraction, which exits through line 150. The first fraction includes oligomer and by-product solvent. The second fraction includes by-product solvent and polymeric by-product.

The second fraction passes through line 150 to TFE 108, which separates the second fraction into a third fraction, which passes to line 183 of solvent flow path 115, and a fourth fraction, which passes from TFE 108 to by-product discharge line 158. From line 158, the fourth fraction may be delivered to a related process, to storage, or to shipment equipment. The third fraction from TFE 108 includes by-product solvent, and the fourth fraction includes hydrocarbons heavier than the by-product solvent, such as the polymeric by-product. Thus, thin film evaporator is operationally configured to separate the by-product solvent from hydrocarbons heavier than the by-product solvent and to provide the by-product solvent to line 183 and to provide the hydrocarbons heavier than the by-product solvent to line 158. For example, the TFE 108 can be operated at a temperature of 90° C. to 150° C. (or 90° C. to 115° C., or 100° C. to 130° C., or 125° C. to 150° C.) and a pressure of 5 psi to 30 psi (or 5 psi to 15 psi, or 10 psi to 25 psi, or 15 psi to 30 psi).

From line 183, by-product solvent of the third fraction enters collection vessel 180. By-product solvent in collection vessel 180 may be called a recycled portion of the by-product solvent. By-product solvent may be continually collected in collection vessel 180 while any one or more of reactors in section 104 remains in the reactor mode. By-product solvent is retained in collection vessel 180 for storage and is prevented from entering reactor section 104, until the time that a selected reactor starts the wash mode of operation. In this way, by-product solvent that is continuously generated can be collected for non-continuous reactor wash cycles. In at least some operations of system 100 and at least some embodiments of reactor section 104, the product stream in line 132, the second fraction in line 150, and the fourth fraction in by-product discharge line 158 each may include a portion of the catalyst, which may be spent or used, appropriate for recycling or disposal.

Continuing to describe the separation section of this process, the first fraction from separation unit 106 passes through line 160 to separation section 110. In separation section 110 the first fraction is separated into a monomer fraction, which exits through line 130 toward reactor 104, a fifth fraction, which exits through product discharge line 170, and a sixth fraction, which exits through line 185 toward collection vessel 180 or discharge line 189. The fifth fraction includes oligomer and passes through line 170. From line 170, the fifth fraction may be delivered to a related process, to storage, or to shipment equipment. Oligomer is an end-product of the operation of system 100. The sixth fraction includes by-product solvent and passes into line 185 of solvent flow path 115. Therefore, passing the first fraction through separation section 110 extracts a portion of the by-product solvent. From line 185, by-product solvent of the sixth fraction may exit system 100 through line 189 as a blow-down stream to purge system 100 of excess by-product solvent or to remove unwanted constituents that may tend to concentrate within the sixth fraction. During operation, at least a portion of the by-product solvent of the sixth fraction in line 185 enters collection vessel 180 and joins the recycled portion of the by-product solvent, which is retained to be recycled to reactor 104.

The monomer fraction includes unreacted monomer from the product stream of line 132. From separation section 110, the monomer fraction passes through reactant return line 130 to be recycled to reactor section 104, joining the feed stream of line 128.

To start the wash mode of operation for a selected reactor, the recycled portion of the by-product solvent stored in collection vessel 180 is delivered to the selected reactor in section 104 via solvent recycle line 187. The by-product solvent delivered from collection vessel 180 may include the portion of the by-product solvent from TFE 108 and/or the portion of the by-product solvent from separation section 110. The recycled by-product solvent flushes reactor section 104 to remove residual material, such as polymeric by-product that may have built-up during the reaction mode of operation. In the wash mode of operation, the flow of feed stream from line 128 and recycled monomer from reactant return line 130 are discontinued to the selected reactor of reactor section 104 that is to be isolated and washed. By including multiple reactor vessels in the reactor section 104, a portion of the reactor section may continue operating in the reaction mode, while an isolated reactor vessel is rinsed. During the wash mode, a purge stream exits from the selected reactor. This purge stream varies in composition and differs from the product stream of a reactor in reaction mode, at least in the relative amounts, the proportions of chemical constituents. In order to minimize the variation in composition leaving reactor section 104 through line 132 the outflow from the select reactor in wash mode is collected in a surge vessel (not shown) and steadily released into line 132 or separation unit 106 to mix with product produced a reactor in the reaction mode. The level in this surge vessel will change, but the outflow from this vessel will remain constant to minimize variations in the total flow from reactor section 104 through line 132. During at least some portion of the wash mode, the purge stream may include oligomer, a by-product solvent, and a polymeric by-product. For at least some embodiments, the purge stream also includes catalyst during at least some portion of the wash mode. As the purge, i.e., the wash mode, continues, the concentration of by-product solvent and a polymeric by-product may increase, and later, concentration of by-product solvent may continue to increase while the polymeric by-product decreases. During the wash mode, various other parts of system 100 continue to operate as previously described.

Figure 2:
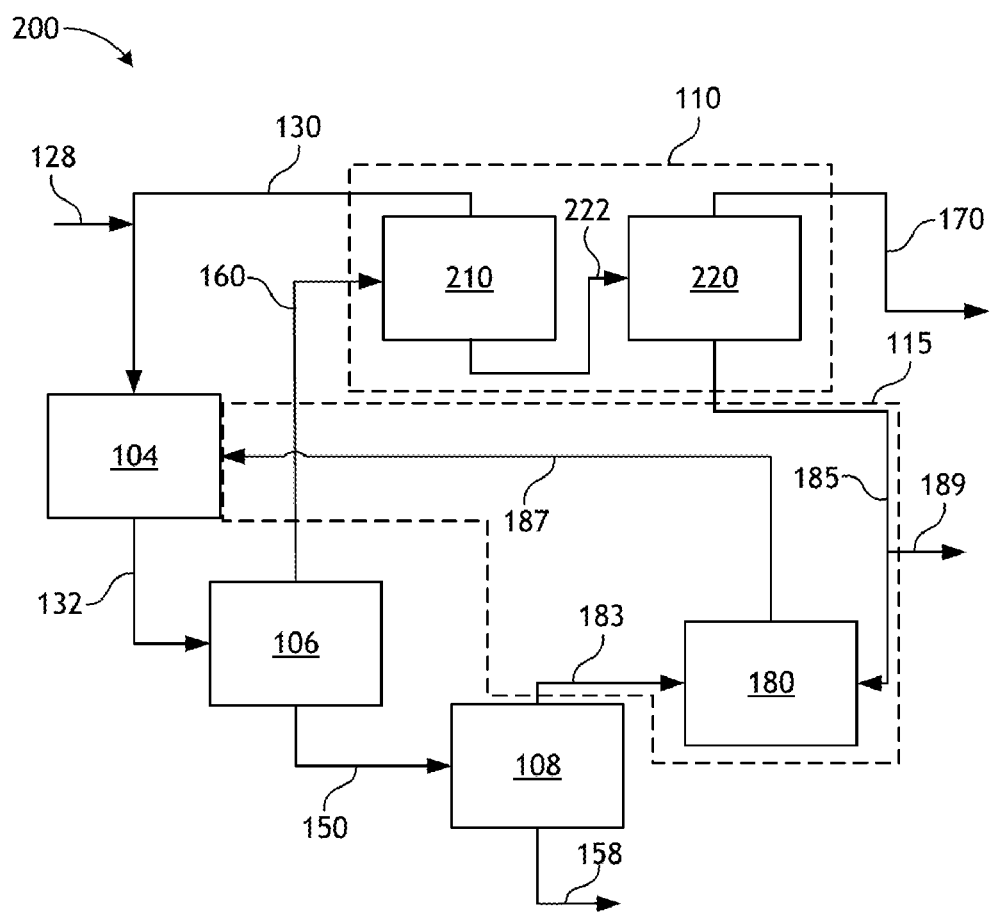
FIG. 2 shows a diagram of another system demonstrating various operations that may be performed in the course of converting monomer to oligomer according to various embodiments of the present disclosure.

FIG. 2 illustrates a system 200 demonstrating various operations that may be performed in the course of converting monomer to oligomer. System 200 is an example of system 100 of FIG. 1. System 200 includes the components described for system 100 and may be modified according to the options described for system 100. System 200 operates in the manner described for system 100. Even so, as will be described here, the specific configuration or operations of some components of system 200 may differ from other examples of system 100.

System 200 includes a reactor section 104 fluidically coupled to a separation unit 106 by a line 132, a thin film evaporator (TFE) 108 fluidically coupled to separation unit 106 by a line 150, a separation section 110 fluidically coupled to separation unit 106 by a line 160 and fluidically coupled to reactor 104 by a reactant return line 130, and a solvent flow path 115 that fluidically couples TFE 108 and separation section 110 to reactor section 104. Solvent flow path 115 includes the components described elsewhere in this disclosure, including a collection vessel 180 and lines 183, 185, and 187, which are fluidically coupled as described elsewhere in this disclosure. A solvent discharge line 189 may fluidically couple solvent flow path 115 to a related process or may lead to storage or shipment equipment. A feed line 128 is fluidically coupled to reactor section 104 and may be fluidically coupled to reactant return line 130. TFE 108 is fluidically coupled to a by-product discharge line 158, which may be fluidically coupled to a related process or may lead to storage or shipment equipment. Separation section 110 is fluidically coupled to a product discharge line 170, which may be fluidically coupled to a related process or may lead to storage or shipment equipment.

Separation section 110 of system 200 includes a plurality of separation units, which in FIG. 2, includes a first separation unit 210 and a second separation unit 220 fluidically coupled to operate in series. First separation unit 210 is fluidically coupled to separation unit 106 by a line 160 and is fluidically coupled to reactor 104 by reactant return line 130. Separation unit 210 is fluidically coupled to second separation unit 220 by a line 222. For discharge of two fluid streams, separation unit 220 is fluidically coupled to discharge line 170 and is fluidically coupled to collection vessel 180 by line 185.

Various aspects or timings of the operation of system 200 may be separated into a reaction mode and a wash mode, as discussed for system 100. In general, during operation, separation unit 210 receives the first fraction of the product stream, which were introduced above in this disclosure, from separation unit 106 via line 160. Separation unit 210 separates the first fraction into a monomer fraction and a heavy fraction, which includes non-polymer products such as oligomer and by-product solvent. Line 130 delivers or recycles the monomer fraction to reactor 104. Line 222 delivers the heavy fraction to separation unit 220. Separation unit 220 separates the heavy fraction from separation unit 210 into the fifth fraction and the sixth fraction, which were introduced above. The fifth fraction includes oligomer, which is an end-product of the system. The fifth fraction passes through product discharge line 170. The sixth fraction includes by-product solvent and passes into line 185 of solvent flow path 115. Therefore, passing the first fraction through separation unit 220 extracts a portion of the by-product solvent. From line 185, by-product solvent of the sixth fraction may exit system 100 through line 189 as a blow-down stream to purge system 100 of excess by-product solvent or to remove unwanted constituents that may tend to concentrate within the sixth fraction. In various modes of operation, at least a portion of the by-product solvent of the sixth fraction in line 185 enters collection vessel 180 and joins into the recycled portion of the by-product solvent, which is retained to be delivered to reactor 104 during the wash mode. Other flows within the vessels and lines of system 200 operate as described for system 100.

Adding more detail to an idea introduced above, in some embodiments, reactor section 104 of a system 100 or 200 includes a plurality of reactors fluidically coupled in parallel with modifications included for at least some of feed line 128, reactant return line 130, line 132, and solvent recycle line 187, to accommodate the plurality of reactors. For example, solvent recycle line 187 may split into multiple solvent recycle lines that separately feed each of the reactors and each of the multiple solvent recycle lines may include a valve to control the flow of solvent therethrough. One or more reactors of reactor section 104 may operate in the wash mode while one or more other reactors of reactor section 104 may operate in the reaction mode simultaneously. As the cycling between an operation and a wash mode occurs for one or more reactors of reactor section 104, the net flow of product from the reactor section remains constant in some examples.

In various embodiments of a system 100 or 200, any of vessels and units, such as reactor 104, separation unit 106, thin film evaporator 108, and collection vessel 180, separation section 110 may be implemented as a plurality of vessels fluidically coupled in parallel or in series. These options were exemplified in system 200; wherein, separation section 110 includes first and second separation units 210, 220. In some embodiments, separation section 110 may comprise more separation units.

Referring to FIGS. 1 and 2, although solvent flow path 115 is configured to blend a by-product solvent discharged by TFE 108 with by-product solvent discharged by separation section 110, some embodiments may include separate solvent flow paths from a thin film evaporate to a reactor and from a separation unit to the reactor or to a different reactor. For various embodiments, separation unit 106 represents a separation section that may include a plurality of separation units, including two to ten separation units, as examples. For various embodiments, thin film evaporator 108 represents a plurality of thin film evaporators (TFEs), including two to ten separation units, as examples.

Referring to FIGS. 1 and 2, from separation unit 106, the first fraction may include from 20 wt % to 90 wt % (preferably 75 wt % to 90 wt %) oligomer and 10 wt % to 50 wt % (preferably 10 wt % to 25 wt %) by-product solvent, and the second fraction may include from 30 wt % to 70 wt % (preferably 50 wt % to 90 wt %) by-product solvent and a corresponding 10 wt % to 70 wt % (preferably 20 wt % to 50 wt %) polymeric by-product. From TFE 108, the third fraction may include 50 wt % or more (preferably 50 wt % to 90 wt % or more preferably 75 wt % to 90 wt %) by-product solvent, and the fourth fraction may include 50 wt % or more (preferably 50 wt % to 90 wt % or more preferably 75 wt % to 95 wt %) polymeric by-product. From separation section 110, the fifth fraction may include 80 wt % or more (preferably 90 wt % to 95 wt % or more preferably 90 wt % to 99 wt %) oligomer, and the sixth fraction may include 50 wt % or more (preferably 50 wt % to 90 wt % or more preferably 75 wt % to 90 wt %) by-product solvent.

Catalytic trimerization of ethylene to produce selectively 1-hexene is a well-known process. Reactants, catalysts, diluents, reaction conditions, and process apparatus configurations are disclosed, for example, in U.S. Pat. Nos. 6,380,451 and 7,157,612 and in U.S. Patent Application Publications 2008/0058486, 2008/0182989, 2008/0188633, 2008/0200626, and 2008/0200743. These documents are incorporated herein by reference.

In the methods disclosed herein, the olefin feed may be ethylene. Ethylene may be oligomerized to form butene (dimerization), hexene (trimerization), octene, decene, and higher-order oligomers. The advantages of this method may also be extended to the dimerization, trimerization, etc., of other olefins, such as propylene, 1-butene, 2-butene, and the like, alone or as part of the reactor feed with ethylene.

Catalyst systems to promote the oligomerization will generally comprise homogeneous, organometallic systems such as single site chromium catalyst systems. Such systems can comprise a chromium source in combination with a heterocyclic, di-aryl, or phosphorus compound such as a pyrrole, pyridyl, or pyridyl-phosphino compound, along with an alkyl aluminum activator such as methyl alumoxane (MAO) or modified methyl alumoxane (MMAO). These and other suitable catalyst systems are well known in the industry.

Oligomerization conditions such as temperature, pressure, flow rates, and residence times are conventional and well known. The reaction temperature may be maintained between about 25° C. and about 150° C., more preferably between about 50° C. and 90° C. The oligomerization reaction is exothermic. The conditions within the reactor may be controlled by evaporative cooling to maintain a desired temperature range. For example, evaporation of the liquid phase and evacuation of the resultant vapor phase, or portions thereof, may withdraw sufficient energy of vaporization from the reactor to maintain a desired temperature. Additionally or alternatively, the desired temperature range may be maintained by introducing excess monomer to maintain a specific rate of evaporation. Additionally or alternatively, the temperature and/or the pressure may be controlled by other means, such as through the use of cooling equipment or pressurization equipment, within the reactor and/or on one or more of the feed streams. Suitable cooling equipment may include, for example, a loop that circulates coolant through a cooling surface inside the reactor and back to a chiller outside the reactor.

The reaction pressure can generally be between about 0 psi (0 kPa) to 1200 psi (8273 kPa), more preferably from about 150 psi (1034 kPa) to about 900 psi (6206 kPa).

The catalyst reaction residence time can generally be about 30 minutes to about 6 hours. Alternatively, the induction period of the catalyst may be longer than 30 minutes and the reactor may be controlled to provide a catalyst reaction residence time of between about 60 minutes and about 6 hours.

EXAMPLE EMBODIMENTS

Embodiment A: A first non-limiting example embodiment is a method comprising, such as a method of converting monomers to oligomers, that method comprising catalytically converting a monomer in a reactor section in a reaction mode in the presence of a catalyst to form a product stream comprising an oligomer, a by-product solvent, and a polymeric by-product; separating the product stream into a first fraction comprising the oligomer and a second fraction comprising a mixture of the by-product solvent and the polymeric by-product; and separating, in a thin film evaporator, the second fraction into a third fraction comprising the by-product solvent and a fourth fraction comprising the polymeric by-product.

Embodiment B: A second non-limiting example embodiment is a system comprising: a reactor section being configurable to operate under oligomerization conditions for a monomer in the presence of a catalyst to form a product mixture comprising an oligomer and a by-product solvent, and a polymeric by-product from the monomer; a separation unit fluidically coupled to receive the product mixture from the reactor; and a thin film evaporator (TFE) fluidically coupled to receive fluid from the separation unit.

Embodiment C: A third non-limiting example embodiment is a method comprising, such as a method of converting monomers to oligomers, that method comprising catalytically converting a monomer in a reactor section in a reaction mode in the presence of a catalyst to form a product stream comprising an oligomer, a by-product solvent, and a polymeric by-product; and separating the product stream into a first fraction and a second fraction; wherein, the first fraction comprises a first portion of the by-product solvent and the oligomer, and the second fraction comprises a second portion of the by-product solvent and the polymeric by-product. The method may further comprise: passing the first fraction through a separation section to extract the first portion of the by-product solvent; passing the second fraction through a thin film evaporator to extract the second portion of the by-product solvent; and delivering the first and second portions of the by-product solvent to the reactor section in a wash mode.

Embodiment A may have one or more of the following additional elements in any suitable combination: Element 1: delivering a recycled portion of the by-product solvent to the reactor section in a wash mode; wherein the recycled portion of the by-product solvent comprises the third fraction; Element 2: wherein the product stream, the second fraction, and the fourth fraction each further comprise at least a portion of the catalyst; Element 3: delivering the recycled portion of the by-product solvent to a collection vessel in the reaction mode; delivering the recycled portion of the by-product from the collection vessel to the reactor section in the wash mode; Element 4: wherein the first fraction further comprises the by-product solvent; and wherein the method further comprises: separating the first fraction into a fifth fraction comprising the oligomer and a sixth fraction comprising the by-product solvent; and wherein the recycled portion of the by-product solvent further comprises the by-product solvent of the sixth fraction; Element 5: wherein separating the first fraction is performed in a separation section comprising: a first separation unit and a second separation unit fluidically coupled in series; wherein the first separation unit is fluidically coupled to receive the first fraction; and wherein the second separation unit is fluidically coupled to the collection vessel to deliver at least a portion of the sixth fraction to the collection vessel; Element 6: wherein the product stream comprises unreacted monomer; and wherein the method further comprises recycling the unreacted monomer to the reactor section; and Element 7: wherein monomer comprises ethylene, and the by-product solvent comprises decene; and wherein the oligomer comprises hexene.

Embodiment B may have one or more of the following additional elements in any suitable combination: Element 8: The system of claim 9 wherein the thin film evaporator is operationally configured to separate the by-product solvent from hydrocarbons heavier than the by-product solvent; Element 9: a solvent flow path extending between the TFE and the reactor section; wherein, the system is operable in a reaction mode wherein by-product solvent in the solvent flow path is prevented from entering the reactor, and the system is operable in a wash mode wherein by-product solvent in the solvent flow path is allowed to enter the reactor section; Element 10: wherein the solvent flow path comprises a collection vessel fluidically coupled between the TFE and the reactor section; Element 11: wherein the solvent flow path extends between the separation section and the reactor section; and Element 12: wherein the solvent flow path comprises a collection vessel fluidically coupled between the TFE and the reactor section and between the separation section and the reactor section.

Embodiment C may have one or more of the following additional elements in any suitable combination: Element 13: wherein the separation section comprises a first separation unit and a second separation unit fluidically coupled in series; wherein the first separation unit is fluidically coupled to receive the first fraction; and wherein the second separation unit is fluidically coupled to the collection vessel to deliver the first portion of the by-product solvent to the collection vessel; Element 14: delivering the first and second portions of the by-product solvent to a collection vessel in the reaction mode; delivering the first and second portions of the by-product solvent from the collection vessel to the reactor section in the wash mode; Element 15: wherein oligomer comprises hexene, and the by-product solvent comprises decene; and Element 16: wherein the monomer is provided to the reactor section continuously as part of a flow process.

Examples of combinations applicable to embodiments A and D include, but are not limited to, Element 1 in combination with one or more of Elements 2-7; Element 2 in combination with one or more of Elements 3-7; Element 3 in combination with one or more of Elements 4-7; and Element 4 in combination with one or more of Elements 5-7.

Examples of combinations applicable to embodiment B include, but are not limited to, Element 8 in combination with one or more of Elements 9-12; Element 9 in combination with one or more of Elements 10-12; Element 10 in combination with one or more of Elements 11-12; and Element 11 in combination with Element 12.

Examples of combinations applicable to embodiment C include, but are not limited to: Element 13 in combination with one or more of Elements 14-16; Element 14 in combination with one or more of Elements 15-16; Element 15 in combination with Element 16.

To facilitate a better understanding of the embodiments of the present invention, the following examples of preferred or representative embodiments are given. In no way should the following examples be read to limit, or to define, the scope of the invention.

EXAMPLES

In the oligomerization of ethylene for the production of 1-hexene, it has been shown that hexene can be produced with 95% selectivity with 4% selectivity to decene and 1% selectivity to polymer. A thin film evaporator available from ROTOTHERM® demonstrated that 92 wt % of the decene could be recovered from a feed similar to the foregoing mixture.

Table 1 provides the mass balance calculated for a system similar to FIG. 2 operating at the ROTOTHERM® demonstrated recovery.

TABLE 1

| | | |
|---|---|---|
| Decene selectivity | 5% | T Decene/T Ethylene |
| Polymer selectivity | 1% | T Polymer/T Ethylene |
| Hexene selectivity | 94% | T Hexene/T Ethylene |
| Ethylene consumption in reactor | 1.06 | T/T Hexene |
| Decene production in reactor | 0.053 | T/T Hexene |
| Polymer production in reactor | 0.011 | T/T Hexene |
| Decene recovery from TFE | 92% | |
| Decene lost with polymer from TFE | 0.016 | T/T Hexene |

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

All numbers and ranges disclosed above may vary by some amount. Whenever a numerical range with a lower limit and an upper limit is disclosed, any number and any included range falling within the range is specifically disclosed. In particular, every range of values (of the form, "from about 'a' to about 'b,'" or, equivalently, "from approximately 'a' to 'b,'" or, equivalently, "from approximately a-b") disclosed herein is to be understood to set forth every number and range encompassed within the broader range of values.

The invention claimed is:

1. A method comprising:
catalytically converting a monomer in a reactor section in a reaction mode in the presence of a catalyst to form a product stream comprising an oligomer, a by-product solvent, and a polymeric by-product;
separating the product stream into a first fraction comprising the oligomer and a second fraction comprising a mixture of the by-product solvent and the polymeric by-product;
separating, in a thin film evaporator, the second fraction into a third fraction comprising the by-product solvent and a fourth fraction comprising the polymeric by-product; and
delivering a recycled portion of the by-product solvent to the reactor section in a wash mode, wherein the recycled portion of the by-product solvent comprises the third fraction.

2. The method of claim 1, wherein the product stream, the second fraction, and the fourth fraction each further comprise at least a portion of the catalyst.

3. The method of claim 1, wherein the delivering includes delivering the recycled portion of the by-product solvent to a collection vessel in the reaction mode, and then from the collection vessel to the reactor section in the wash mode.

4. The method of claim 1, wherein the first fraction comprises further comprises the by-product solvent; and wherein the method further comprises:
separating the first fraction into a fifth fraction comprising the oligomer and a sixth fraction comprising the by-product solvent; and
wherein the recycled portion of the by-product solvent further comprises the by-product solvent of the sixth fraction.

5. The method of claim 4, wherein separating the first fraction is performed in a separation section comprising a first separation unit and a second separation unit fluidically coupled in series;
wherein the first separation unit is fluidically coupled to receive the first fraction; and
wherein the second separation unit is fluidically coupled to the collection vessel to deliver at least a portion of sixth fraction to the collection vessel.

6. The method of claim 1, wherein the product stream comprises unreacted monomer; and wherein the method further comprises recycling the unreacted monomer to the reactor section.

7. The method of claim 1, wherein monomer comprises ethylene, and the by-product solvent comprises decene; and wherein the oligomer comprises hexene.

8. A system comprising:
a reactor section that operates under oligomerization conditions for a monomer in the presence of a catalyst to form a product mixture comprising an oligomer and a by-product solvent, and a polymeric by-product from the monomer;
a separation unit fluidically coupled to receive the product mixture from the reactor, wherein the separation unit separates the product mixture into a first fraction comprising the oligomer and second fraction comprising a mixture of the by-product solvent and the polymeric by-product;
a thin film evaporator (TFE) fluidically coupled to receive the second fraction from the separation unit, wherein the TFE separates the second fraction into a third fraction comprising the by-product solvent and a fourth fraction comprising the polymeric by-product; and
a solvent flow path that is fluidically coupled to receive the by-product solvent and provide the by-product solvent to the reactor section,
wherein when the system is in a reaction mode, the by-product solvent in the solvent flow path is prevented from entering the reactor, and when the system is in a wash mode, the by-product solvent in the solvent flow path enters the reactor section.

9. The system of any claim 8, wherein the solvent flow path comprises a collection vessel fluidically coupled between the TFE and the reactor section.

10. The system of any claim 8, wherein the solvent flow path extends between the separation section and the reactor section.

11. The system of any claim 8, wherein the solvent flow path comprises a collection vessel fluidically coupled between the TFE and the reactor section and between the separation section and the reactor section.

12. A method comprising:
catalytically converting a monomer in a reactor section in a reaction mode in the presence of a catalyst to form a product stream comprising an oligomer, a by-product solvent, and a polymeric by-product; and
separating the product stream into a first fraction and a second fraction;
wherein the first fraction comprises a first portion of the by-product solvent and the oligomer; and wherein the second fraction comprises a second portion of the by-product solvent and the polymeric by-product;
passing the first fraction through a separation section to separate the first portion of the by-product solvent;
passing the second fraction through a thin film evaporator to separate the second portion of the by-product solvent; and
delivering the first and second portions of the by-product solvent to the reactor section in a wash mode.

13. The method of claim 12, wherein the separation section comprises a first separation unit and a second separation unit fluidically coupled in series; wherein the first separation unit is fluidically coupled to receive the first fraction; and wherein the second separation unit is fluidically coupled to the collection vessel to deliver the first portion of the by-product solvent to the collection vessel.

14. The method of any claim 12, further comprising:
delivering the first and second portions of the by-product solvent to a collection vessel in the reaction mode; and
delivering the first and second portions of the by-product solvent from the collection vessel to the reactor section in the wash mode.

15. The method of any claim 12, wherein oligomer comprises hexene, and the by-product solvent comprises decene.

16. The method of any claim 12, wherein the monomer is provided to the reactor section continuously as part of a flow process.

* * * * *